US00PP10722P

United States Patent [19]

Hammond

[11] Patent Number: Plant 10,722

[45] Date of Patent: Dec. 15, 1998

[54] *ARGYRANTHEMUM FRUTESCENS* CULTIVAR NAMED 'PRIMROSE PETITE'

[76] Inventor: Frank Hammond, 100 Boundary Road, Narre Warren East, Victoria, 3804, Australia

[21] Appl. No.: 848,790

[22] Filed: May 1, 1997

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 10,298 3/1998 Cunneen ..... Plt./68.1

OTHER PUBLICATIONS

GTITM UPOV–ROM Citation for 'Primrose Petite' as per Au PBR 95017, Mar. 12, 1997.

GTITM UPOV–ROM Citation for 'Primrose Petite' as Per NZ PBR CHR014, Oct. 14, 1996.

*Primary Examiner*—Howard J. Locker

*Assistant Examiner*—Kent L. Bell

[57] ABSTRACT

A new and distinct selection of Silver Flower which shall be referred hereinafter as *Argyranthemum frutescens* cultivar 'Primrose Petite'. *Argyranthemum frutescens* cultivar 'Primrose Petite' differs distinctively from other *Argyranthemum frutescens* plants by its unique combination of dense, low uniform growth habit with short grey foliage and lemon yellow bloom color.

1 Drawing Sheet

BACKGROUND OF THE INVENTON

This invention relates to a new and distinct selection of *Argyranthemum frutescens* (L.) Schutz-Bip., native to the Canary Islands and a member of the Compositae family. *Argyranthemum frutescens* cv. 'Primrose Petite' was the result of an uncontrolled open pollinated seed. The seed parent was *Argyranthemum frutescens* cv. 'Harvest Gold', however, the pollen parent was unknown. I selected this seedling in October 1995. My discovery was made at 100 Boundary Road, Narre Warren East, Victoria, Australia. Selection was based on the dense uniform growth with short grey foliage and lemon yellow bloom color. My new plant has been asexually reproduced by cutting since the discovery in 1995 at 100 Boundary Road, Narre Warren East, Victoria, Australia and later at Monrovia Nursery Company, 18331 E. Foothill Boulevard, Azusa, Calif. Had this seedling not been discovered and propagated it may have been lost to mankind. It is unlikely these particular select and favorable attributes of this plant could be conveyed to progeny through sexual reproduction in the next generation. However, through extensive propagation by rooting of the plant it has been established that the novel exceptional characteristics of this plant are stable and reliably passed on to clonal specimens through asexual reproduction.

SUMMARY OF THE INVENTION

*Argyranthemum frutescens* cv. 'Primrose Petite' has a dense low uniform growth habit. It clearly appears to have a ground hugging habit. When compared to four other named selections (cv. Annabel (U.S. Plant Pat. application Ser. No. 08/851,475), cv. Blanche (U.S. Plant Pat. application No. 08/846,476), cv. Gretel (U.S. Plant Pat. application Ser. No. 08/846,475), cv. Carmella (U.S. Plant Pat. application Ser. No. 08/846,477) at seven months of age in Azusa, Calif., the foliage of cultivar 'Primrose Petite' is only 9 cm high whereas other selections range 20–24 cm in height. This low habit does not appear to become shrub like and instead remains more flat topped. As a result of this growth the overall flowering arrangement is also in a somewhat flat arrangement. A seven month old container plant in full flower exhibits a height inclusive of flowers of 15 cm tapering only to 12 cm on the edges of the plant. This is a totally different habit from the above mentioned cultivars which exhibit a rounded subshrub habit.

Ultimately my selection will achieve a height of 22.3 cm with a 1.3 cm deviation. This is the shortest of the selections compared and has the smallest deviation in uniformity of height.

The lemon yellow bloom color is nicely set above the thick grey-green foliage giving an overall chartreuse look to the plant.

*Argyranthemum frutescens* 'Primrose Petite' has tolerated a minus five degree Celsius temperature which is equivalent to a USDA hardiness zone seven with no harm or damage. Winter protection is necessary from heavy frost.

BRIEF DESCRIPTION OF ILLUSTRATION

The accompanying photograph shows my selection in bloom. The color is consistent with no significant flower color fading with age.

BOTANICAL DESCRIPTION

Below is a detailed description of *Argyranthemum frutescens* cultivar 'Primrose Petite', the color terminology is from the British Horticultural Color Charts. Measurements are based on 20 random samples taken in Australia.

*Overall habit*.—Perennial, low subshrub.

Overall size: Almost twice as wide than tall.

*Height*.—22.3 cm (±1.3 cm).

*Width*.—40.2 cm (±4.0 cm).

Bloom season in Australia: Heaviest bloom in Spring for 10 weeks.

*Melbourne*.—6–8 months per year does not flower in winter.

*Brisbane*.—4–6 months per year does not flower in summer.

Foliage:

*Bloom lastingness*.—7 to 14 days per flower.

*Stem*.—Coloration Spinach Green 0960/3 to 0960/2.

*Arrangement*.—Alternate.

*Surface*.—Upper: glabrous. Lower: glabrous.

*Shape*.—Pinnatisect, primary segment, 3–5.

*Margins*.—Vary from deeply to lighted lobed, lobes end with mucronulate tip.

*Size*.—Length: 42.7 mm (±4.7 mm). Width: 27.2 mm (±3.5 mm).

*Color*.—Upper and lower leaf surface: Both sides are Leek Green 000858.

*Texture*.—Thick, succulent.

Inflorescences:

*Bud shape*.—Globose.

*Bud Length*.—8 mm.

*Bud width*.—8 mm.

*Bud color*.—Scheeles Green 860/2. Paper like bracts Mars Orange 013/3 with tint of Maroon 1030/5.

*Diameter*.—3.5 cm to 4.0 cm.

*Arrangement*.—Heterogamus capitula, 1 per peduncle.

*Peduncle length*.—3.5 cm to 5.5 cm.

*Disc color*.—Barium Yellow 503/0.

*Disc head diameter*.—11.8 mm (±0.8 mm).

*Ray floret number*.—Average 20–23.

*Disc floret reproductive organs*.—Pistillate and staminate organs present.

*Ray floret reproductive organs*.—Pistillate organs present.

*Ray floret upper surface color*.—Dresden Yellow 64/3, no fading with age.

*Ray floret undersurface color*.—Mimosa Yellow 602/3, no fading with age.

*Ray floret aspect*.—Flattened at right angles to peduncle at full anthesis.

*Ray floret shape*.—Ligulate.

*Ray floret length*.—18 mm to 20 mm.

*Ray floret width*.—6 mm 7 mm.

*Basal line or spot*.—Absent.

*Fruit*.—A 2–4 angled cypsela, winged.

*Fragrance*.—Faint light scent.

Disease resistance: The rust diseases of the genera Coleosporium and Cronartium are not known to occur on my selection in Australia.

I claim:

1. A new and distinct *Argyranthemum frutescens* plant substantially as shown and described which differs distinctively from other *Argyranthemum frutescens* plants by its unique combination of a dense, low uniform growth habit with short grey foliage and lemon yellow bloom color.

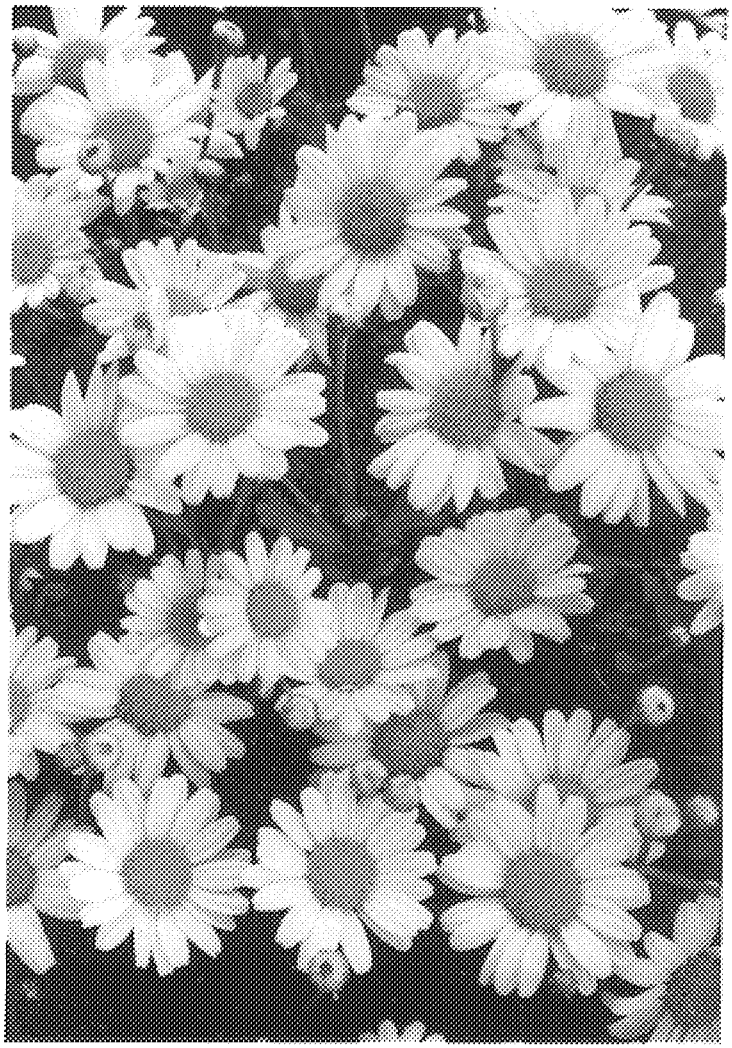

* * * * *